US006884908B2

(12) United States Patent
Srivastava et al.

(10) Patent No.: US 6,884,908 B2
(45) Date of Patent: Apr. 26, 2005

(54) **PROCESS FOR ISOLATION OF HEPATOPROTECTIVE AGENT "OLEANOLIC ACID" FROM *LANTANA CAMERA***

(75) Inventors: Santosh Kumar Srivastava, Lucknow (IN); Merajuddin Khan, Lucknow (IN); Suman Preet Singh Khanuja, Lucknow (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 10/815,095

(22) Filed: Mar. 30, 2004

(65) Prior Publication Data

US 2004/0220425 A1 Nov. 4, 2004

(30) Foreign Application Priority Data

Mar. 31, 2003 (IN) .................................... 534/DEL/2003

(51) Int. Cl.[7] ................................................ C07C 61/12
(52) U.S. Cl. ....................................................... 562/498
(58) Field of Search .......................................... 562/498

(56) References Cited

PUBLICATIONS

Misra et al , High concentration of hepatoprotective oleanolic acid and its derivatives in the *Lantana camara* roots, Feb. 1997, Planta Medica, 63: p. 584.*

* cited by examiner

*Primary Examiner*—Cecilia J. Tsang
*Assistant Examiner*—Taylor Victor Oh
(74) *Attorney, Agent, or Firm*—Weingarten, Schurgin, Gagnebin & Lebovici LLP

(57) ABSTRACT

Accordingly the present invention provides an improved and economical process for the isolation of oleanolic acid from the roots of *Lantana camara*, which comprises of drying, grinding and defattening of *Lantana camara* roots with light petroleum followed by over night extractions at room temperature (30–40° C.) three times with a single solvent selected from $CH_2Cl_2$, $CHCl_3$, EtOAc, ether, acetone, MeOH, EtOH etc., removal of solvent under vacuum at 35–45° C., precipitation of crude extract and repeated partial crystallization of precipitate with a single solvent selected from $CH_2Cl_2$, $CHCl_3$, EtOAc, ether, acetone, MeOH, EtOH, $H_2O$ and others resulting in the isolation of oleanolic acid with 1% yield.

5 Claims, No Drawings

PROCESS FOR ISOLATION OF HEPATOPROTECTIVE AGENT "OLEANOLIC ACID" FROM *LANTANA CAMERA*

This application claims priority to an Indian application No. 534/Del/2003 filed Mar. 31, 2003.

1. Field of Invention

The present invention relates to an improved and economical process for the isolation of hepatoprotective agent "oleanolic acid" from *Lantana camara.*

2. Background and Prior Art

Oleanolic acid [(3-O-β-hydroxy-olea-12-en-28-oic acid is a triterpenoid compound, which exist widely in natural plants in the form of free acid or aglycones for triterpenoid saponins. Oleanolic acid has been isolated from more than 120 plant species. It has been identified as the main bioactive constituent of the medicinal plants used in folk medicine such as *Aralia chinensis*, var. nuda nakai, *Beta vulgaris* L. var. cicla L., *Swertia mileensis, Swertia japonica, Tetraponax papyriferum, Panax ginseng* used in hepatoprotection; *Ligustrum lucidum, Luffa cyclindrica, Oleandra neriifolia, Sapindus mulcorossi* used in anti-inflammation and *Gonoderma lucidum* and *Glechoma hederacea* used for anticarcinogenic activity and antitumor promotion. Oleanolic acid, as such has been reported to exhibit potent hepotoprotective activity. It decreases $CCl_4$-induced liver parenchymal cell necrosis, steatosis and degeneration plus alcohol-induced chronic cirrhosis. It is as such marketed in China for human hepatitis. Similarly oleanolic acid has also shown significant anti-inflammatory activity by inhibiting raw paw edema produced by dextran and by suppressing adjuvant induced arthritis in rats and mice. It is also important to note that oleanolic acid also inhibits tumor initiation and tumor promotion. Treatment of rats with oleanolic acid (200 ppm) in diet for 3 weeks decreases the incidence and multiplicity of azoxymethane-induced intestinal tumor. Oleanolic acid also showed significant hypolipidemic and anti-atherosclerotic properties. Treatment of experimental hyperlipidemic rats with oleanolic acid (50 mg/kg, P.O. for 9 days) decreases the elevated blood cholesterol and β-lipoprotein levels by more than 40%. Cosmetic and pharmaceutical preparations of oleanolic have been patented in Japan for use in skin care and non-lymphatic leukemia.

Apart from the above, oleanolic acid has also shown antiulcer, antimicrobial, hypoglycaemic activity, protection against cyclophosphamide induced toxicity, anticarcinogenic and antifertility activities etc. It was observed that although oleanolic acid has been isolated from more than 120 plant species however, due to the poor yield and tedious column chromatographic separation procedures of the bioactive constituent from *Panax ginseng, Aralia chinensis, Eugenia Jaumbolana, Calendula officinalis, Gonoderma lucidum, Oleandra neriifolia* (Plants used in folk medicines) and most of the other plant species, this bioactive constituent has become an expensive pharmaceutical compound. This prompted us to search for an inexpensive, easily available, wildly growing and rich source of oleanolic acid and develop an easy and economical process for the isolation of this important therapeutic agent so that it can be brought under the reach of common masses.

On going through the literature, it was observed that sugar beets may be an inexpensive, easily available source of oleanolic acid. An extraction procedure for oleanolic acid has also been patented from Sugar beet ("Extraction of oleanolic acid from Sugar beets for treatment of liver failure", Yabuchi et al. 1988, chemical Abstract 108, 82082p; Yabuchi et al, 1987, Japanese pat. No. 62126149). This process involves crude oleanolic acid preparation from 1 Kg each of sugar beet roots and leaves. For further purification, the crude preparations were extracted with. MeOH, treated with HCl, and subjected to column chromatographic separation. The recovery rate from crude preparation was only 66.3%.

The method described above suffers from a number of disadvantages. The major disadvantage of the above method is the very low (exact yield not available) concentration of oleanolic acid saponin in both leaf and roots of sugar beets. The second disadvantage of the above process is that oleanolic acid has not been isolated as such, but was obtained after an extra and tedious acid hydrolysis step, which reduces the recovery of bioactive constituent by almost 33%. The third major disadvantage of the above process is that it utilizes column chromatographic separation for the isolation of oleanolic acid using various mixture of eluting solvents. Thus resulting in a tedious, time taking and expensive process for the isolation of oleanolic acid.

The other inexpensive, easily available and rich source of oleanolic acid is roots of *Lantana camara. L. camara* is a prickly climbing aromatic shrub of the family Verbenaceae. It is native to tropical America and was introduced in India as an ornamental and hedge plant, but now it has been completely naturalized and growing very wildly throughout India. A dense wild population of this shrub can be easily seen along the railway lines, forests and in almost all the wild places. It has also been recorded that different parts of the plant are rich source of various bioactive principles. In Africa, infusion of the leaves are used against rheumatism, asthama, cough and colds. The whole plant and its infusions are considered to be anti-pyretic, diaphoretic and anti-malarial. Recently an isolation procedure for oleanolic acid has been patented from the rootlets and root bark of *L. camara* ("High concentration of hepatoprotective oleanolic acid and its derivatives in *Lantana camara* roots", Misra et al. 1997, *Planta Med.* 63: 582, Misra et al. 1996, *Indian Pat.* No.184489). This process involves extraction of rootlets and root bark with a mixture of three solvents. The crude so obtained is chromatographed on silica gel column and the oleanolic acid rich fractions are further purified on another column, thus resulting in the isolation of 1.47% of oleanolic acid.

The method described above suffers from a number of disadvantages. The biggest disadvantage of the above method is that it uses rootlets and root barks of *L. camara*. The rootlets are very small and few in *L. camara*, hence can not be obtained in sufficient amount for commercial purpose. Similarly the roots of *L. camara* are also small in size and are covered with very thin bark, hence peeling off the bark on commercial scale is neither possible nor it will be economical. It has been observed that rootlets and root barks in *L. camara* constitute not more than 20% of the total roots. Hence for obtaining 3.75 Kg of rootlets and root bark, 18.75 Kg of roots would have been certainly used, which gave only 55 g of oleanolic acid in the above process. But if 18.75 Kg of *L. camara* roots are processed according to our method it will give ~187.5 g of oleanolic acid. In this way it is very clear that the yield of oleanolic acid by our process is 3.4 times more than the above process.

The second disadvantage of the above process is that it utilizes mixture of three solvents for the extraction of plant material, which neither can be used again nor can be recycled. The third major disadvantage of the above process is that it utilizes repeated column chromatography on silica gel for the isolation of oleanolic acid using mixtures of eluting solvents, thus resulting in a tedious, time taking and enormous expensive procedure, which can not be economically viable.

OBJECT OF THE INVENTION

The main object of the present invention is to provide an improved economical process for the isolation of oleanolic acid directly from the roots of *L. camara*, which obiates the draw backs of the existing processes.

Another object of the present invention is to completely avoid use of highly tedious, time taking column chomatographic purification process for the isolation of oleanolic acid from the roots of *Lantana camara*.

Still another object of the present invention is to provide an economical process for the isolation of oleanolic acid from the roots of *Lantana camara*.

Another object of the present invention is that it completely omit the use of highly tedious, time taking and expensive repeated column chromatographic purification process used in prior art processes.

Another object of the present invention is that it directly uses roots while the existing processes use only rootlets and root bark, resulting in a yield advantages of 3.4 times. Another object of the present invention single solvent can be used for the extraction of oleanolic acid the plant material, which can be reused and/or recycled However, the prior art process uses mixture of three solvents, which can neither be reused nor can be recycled.

Still another object of the present invention is that this process uses simple precipitation and crystallization processes for the isolation of oleanolic acid which are easy, less time taking and highly inexpensive.

SUMMARY OF THE INVENTION

Accordingly the present invention provides an improved and economical process for the isolation of oleanolic acid from the roots of *Lantana camara*, which comprises of drying, grinding and defattening of *Lantana camara* roots with light petroleum followed by over night extractions at room temperature (30–40° C.) three times with a single solvent selected from $CH_2Cl_2$, $CHCl_3$, EtOAc, ether, acetone, MeOH, EtOH etc., removal of solvent under vacuum at 35–45° C., precipitation of crude extract and repeated partial crystallization of precipitate with a single solvent selected from $CH_2Cl_2$, $CHCl_3$, EtOAc, ether, acetone, MeOH, EtOH, $H_2O$ and others resulting in the isolation of oleanolic acid with 1% yield.

DETAILED DESCRIPTION OF THE INVENTION

Accordingly the present invention provides an improved and economical process for the isolation of oleanolic acid from the roots of *Lantana camara*, which comprises of drying, grinding and defattening of *Lantana camara* roots with light petroleum followed by over night extractions at room temperature (30–40° C.) three times with a single solvent selected from $CH_2Cl_2$, $CHCl_3$, EtOAc, ether, acetone, MeOH, EtOH etc., removal of solvent under vacuum at 35–45° C., precipitation of crude extract and repeated partial crystallization of precipitate with a single solvent selected from $CH_2Cl_2$, $CHCl_3$, EtOAc, ether, acetone, MeOH, EtOH, $H_2O$ and others resulting in the isolation of oleanolic acid with 1% yield.

In an embodiment of the present invention a varied range of defattening solvents petroleum ether, hexane, benzene, toluene and dichloromethane can be used.

In another embodiment of the present invention a varied range of fractionating solvents $CH_2Cl_2$, $CHCl_3$, EtOAc, ether, actone, MeOH, and EtOH can be used.

Still in another embodiment of the present invention a varied range of precipitating and crystallizing solvents $CH_2Cl_2$, $CH_3CHCl_2$, $CHCl_3$, EtOAc, ether, actone, MeOH, EtOH and $H_2O$ can be used.

In another embodiment of the present invention which completely omit the use of highly tedious, time taking and expensive repeated column chromatographic purification process used in prior art processes.

In another embodiment of the present invention which directly uses roots while the existing processes use only rootlets and root bark, resulting in a yield advantages of 3.4 times.

In another embodiment of the present invention wherein single solvent can be used for the extraction of oleanolic acid the plant material, which can be reused and/or recycled However, the prior art process uses mixture of three solvents, which can neither be reused nor can be recycled.

In another embodiment of the present invention uses simple precipitation and crystallization processes for the isolation of oleanolic acid which are easy, less time taking and highly inexpensive.

EXAMPLES

The following examples are given by way of illustration of the present invention and should not be construed to limit the scope of present invention.

Example—1

The fresh *Lantana camara* roots were collected from the field. The roots were first washed and made free from soil and other organic matters. The clean roots were chopped into small pieces and shade dried. The dried roots were powdered in a grinder. The powdered *Lantana camara* roots (700 g) were first hot defatted with petroleum ether (bp 40–60° C. and then extracted with dichloromethane ($CH_2Cl_2$). The extraction was carried out for 8 hrs till the material was completely exhausted. Removal of the solvent under vacuum at 40° C. gave a brownish viscous mass. This was dissolved in excess of water and left over night at room temperature. The precipitate so obtained was filtered and the precipitate was crystallized with ether four times, which resulted in the isolation of oleanolic acid in 0.7% yield.

Example—2

The powdered roots (2 Kg) were first cold defatted with hexane and then extracted with MeOH over night four times at room temperature. Removal of the solvent was carried out under vacuum at 40° C. The crude extract was dissolved in excess of EtOAC and left overnight at room temperature. The precipitate was filtered and crystallized with MeOH. Precipitation and crystallization processes were repeated 4 times, which resulted in the isolation of oleanolic acid in 0.85% yield.

Example—3

The powdered roots (1.5 Kg) were first hot defatted with petroleum ether (bp 40–60° C.) and then extracted with acetone. The extraction areas carried out for about 8 hrs till the material was completely exhausted. Removal of the solvent under vacuum at 40° C. gave a brownish viscous mass. This was dissolved in excess of dichloromethane by heating and then left over night at room temperature. The precipitate so obtained was filtered and crystallized with ether thrice, which resulted in the isolation of oleanolic acid in 0.65% yield.

Example —4

The powdered roots (3 Kg) were first cold defatted thrice with petroleum ether (bp 40–60° C.) at room temperature over night. The defatted material was then extracted with $CHCl_3$ four times at room temperature over night. Removal of the solvent was carried out under vacuum at 40° C. The crude extract so obtained was dissolved in acetone and left over night for precipitation. The precipitate so obtained was filtered and crystallized with EtOH. Precipitation and crystallization process were repeated 4 times which gave oleanolic acid in 0.8% yield.

Example —5

The powdered roots of *L. camara* (5 Kg) were defatted with hexane in cold thrice at room temperature. The defatted material was then extracted with EtOAc four times overnight at room temperature. The solvent was removed under vacuum at 40° C. and the crude extract so obtained was dissolved in ether and left over night in refrigerator for precipitation. The precipitate so obtained was filtered and dissolved in MeOH for crystallization. Precipitation and crystallization process were repeated for 4 times, which gave oleanolic acid in 0.7% yield.

Example —6

The powdered roots of *L. camara* (10 Kg) were defatted thrice in cold overnight with petroleum ether (bp 40–60° C.) and then extracted exhaustively with EtOH four times overnight at room temperature. The solvent was removed under vacuum at 40° C. and the crude was dissolved in $CHCl_3$ and left overnight for precipitation. The precipitate so obtained was crystallized with MeOH. Precipitation and crystallization process were repeated 4 times, which gave oleanolic acid in 0.9% yield.

ADVANTAGES

1. The main advantage of our process is that it completely omit the use of highly tedious, time taking and expensive repeated column chromatographic purification process used in prior art processes.
2. The other major advantage of our process is that it directly uses roots while the existing processes use only rootlets and root bark, resulting in a yield advantages of 3.4 times.
3. Single solvent can be used for the extraction of oleanolic acid the plant material, which can be reused and/or recycled However, the prior art process uses mixture of three solvents, which can neither be reused nor can be recycled.
4. The present process uses simple precipitation and crystallization processes for the isolation of oleanolic acid which are easy, less time taking and highly inexpensive.

We claim:

1. A process for the isolation of oleanolic acid from the roots of *Lantana camara*, said process comprising the steps:

a) obtaining the dried root of *Lantana camara,* b) grinding the dried root of step (a) to obtain root powder, c) defattening the root powder with organic solvent for a period in the range of 6–12 hours at a temperature in the range of 30–40° C. three times with a solvent, d) extracting the defattened root powder for a period in the range of 6 to 12 hours, at a temperature in the range of 30–40° C. three times with a solvent, e) removing solvent from root powder and solvent mixture to obtain the crude extract, and f) precipitating the crude extract followed by repeated partial crystallization of precipitate with a solvent to obtain the oleanolic acid.

2. A process as claimed in claim 1, wherein in step (c) and (d) the solvent used is selected from a group comprising petroleum spirit, hexane, benzene, toluene and dichloromethane etc.

3. A process as claimed in claim 1, wherein in step (e) the solvent removal is carried out under vacuum at a temperature in the range of 35 to 45° C.

4. A process as claimed in claim 1, wherein in step (f) the precipitating and crystallizing solvents are selected from a group comprising dichloromethane, dichloroethane, chloroform, ethylacetate, diethyl ether, acetone, methanol, ethanol and $H_2O$.

5. A process as claimed in claim 1, wherein the yield of olenolic acid is 1%.

* * * * *

UNITED STATES PATENT AND TRADEMARK OFFICE

CERTIFICATE OF CORRECTION

PATENT NO. : 6,884,908 B2
APPLICATION NO. : 10/815095
DATED : April 26, 2005
INVENTOR(S) : Santosh Kumar Srivastava et al.

It is certified that error appears in the above-identified patent and that said Letters Patent is hereby corrected as shown below:

Front Page, Title (54), “CAMERA” should read --CAMARA--; and

Column 1, line 4, “CAMERA” should read --CAMARA--.

Signed and Sealed this

Seventh Day of November, 2006

JON W. DUDAS
*Director of the United States Patent and Trademark Office*